United States Patent
Mul et al.

(10) Patent No.: US 6,392,066 B1
(45) Date of Patent: May 21, 2002

(54) EPOXIDATION OF OLEFINS USING LANTHANIDE-PROMOTED SILVER CATALYSTS

(75) Inventors: Guido Mul, Nootdorp (NL); Marianna F. Asaro, Belmont, CA (US); Albert S. Hirschon, Menlo Park, CA (US); Robert B. Wilson, Jr., Palo Alto, CA (US)

(73) Assignee: SRI International, Menlo Park, CA (US)

(*) Notice: Subject to any disclaimer, the term of this patent is extended or adjusted under 35 U.S.C. 154(b) by 0 days.

(21) Appl. No.: 09/791,904

(22) Filed: Feb. 22, 2001

(51) Int. Cl.[7] .................... C07D 301/10; C07D 301/03
(52) U.S. Cl. ................. 549/534; 549/536; 502/303
(58) Field of Search ................. 549/534, 536; 502/303

(56) References Cited

U.S. PATENT DOCUMENTS

| | | | |
|---|---|---|---|
| 3,836,481 A | 9/1974 | Kajimoto et al. | 252/462 |
| 4,010,115 A | 3/1977 | Nielsen et al. | 252/454 |
| 4,248,740 A | 2/1981 | Mitsuhata et al. | 252/463 |
| 4,342,667 A | 8/1982 | Armstrong et al. | 252/476 |
| 4,845,253 A | 7/1989 | Bowman | 549/536 |
| 5,112,795 A | 5/1992 | Minahan et al. | 502/324 |
| 5,504,053 A | 4/1996 | Chou et al. | 502/348 |
| 5,597,773 A | 1/1997 | Evans et al. | 502/348 |
| 5,618,954 A | 4/1997 | Boeck et al. | 549/534 |
| 5,625,084 A | 4/1997 | Pitchai et al. | 549/536 |
| 5,686,380 A | 11/1997 | Pitchai et al. | 502/347 |
| 5,703,254 A | 12/1997 | Gaffney et al. | 549/536 |
| 5,763,630 A | 6/1998 | Kahn et al. | 549/534 |
| 5,770,746 A | 6/1998 | Cooker et al. | 549/534 |
| 5,780,657 A | 7/1998 | Cooker et al. | 549/534 |
| 5,856,534 A | 1/1999 | Cooker et al. | 549/534 |
| 5,861,519 A | 1/1999 | Kahn et al. | 549/536 |
| 5,864,047 A | 1/1999 | Gaffney | 549/536 |
| 5,939,569 A | 8/1999 | Jones et al. | 549/512 |

FOREIGN PATENT DOCUMENTS

| | | |
|---|---|---|
| CA | 1282772 | 4/1991 |
| JP | 50112292 | 9/1975 |

OTHER PUBLICATIONS

Breitscheidel et al. (1991), "Metal Complexes in Inorganic Matrices. 7.[1] Nanometer–Sized, Uniform Metal Particles in a $SiO_2$ Matrix by Sol–Gel Processing of Metal Complexes," *Chem. Mater.* 3(3):559–566.

Geenen et al. (1982), "A Study of the Vapor–Phase Epoxidation of Propylene and Ethylene on Silver and Silver–Gold Alloy Catalysts," *Journal of Catalysis* 77:499–510.

Giordano et al. (1981), "Epoxidation of Ethylene on Silver-–Loaded Zeolites," *Zeitschrift für Physikalische Chemie Neue Folge, Bd.* 127:109–124.

Jacobs et al. (1979), "Some Unusual Properties of Activated and Reduced AgNaA Zeolites," *Journal of the Chemical Society* 1:56–64.

Sachtler et al. (1981), "On the Mechanism of Ethylene Epoxidation," *Catalysis Reviews, Science and Engineering* 23 (1&2):127–149.

Toreis et al. (1987), "The Oxidation of Ethylene Over Silver–Based Alloy Catalysts," *Journal of Catalysis* 108:161–174.

Wang et al. (1995), "The Effect of Chloride Ions on a $Li^+$–MgO Catalyst for the Oxidative Dehydrogenation of Ethane," *Journal of Catalysis* 151: 155–167.

Primary Examiner—Amelia Owens
(74) Attorney, Agent, or Firm—J. Elin Hartrum; Reed & Associates

(57) ABSTRACT

A process is provided for use in the epoxidation of olefins, having particular utility in the epoxidation of propylene to form propylene oxide, using a lanthanide-promoted, supported, silver catalyst prepared via precipitation. A preferred embodiment uses silver nitrate and lanthanum nitrate to form the catalyst on a $BaCO_3$ support.

34 Claims, 1 Drawing Sheet

EPOXIDATION OF OLEFINS USING LANTHANIDE-PROMOTED SILVER CATALYSTS

TECHNICAL FIELD

Figure 1:
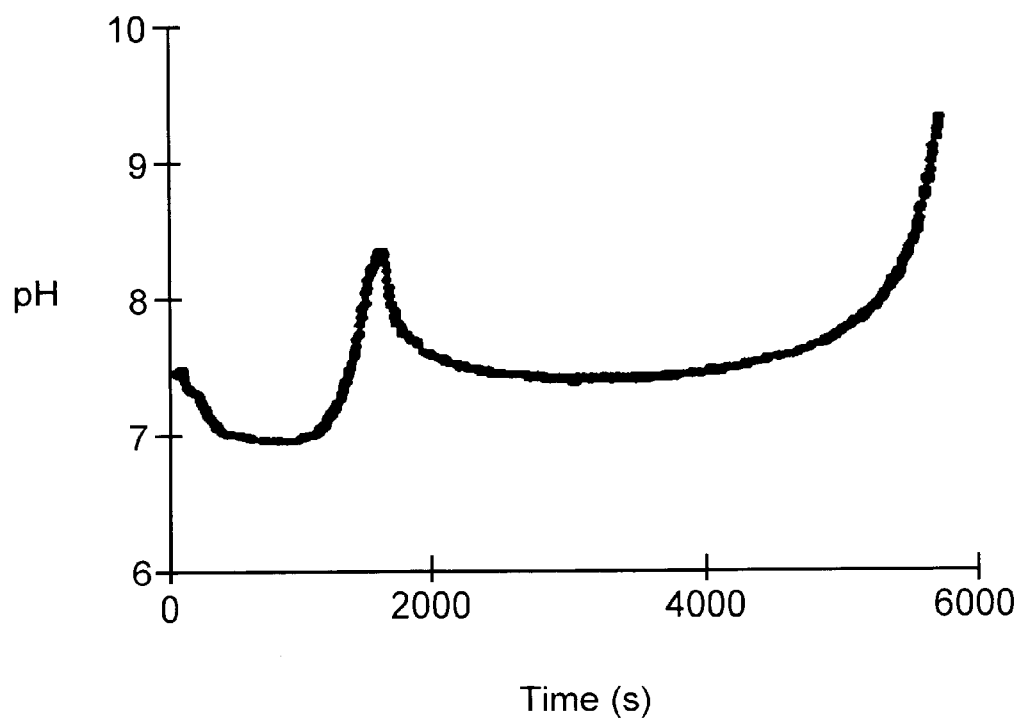

This invention relates generally to novel catalysts for use in the epoxidation of olefins, having particular utility in the epoxidation of propylene to give propylene oxide. The catalyst is prepared via precipitation and is a lanthanide-promoted, supported silver catalyst. The invention also relates to methods for catalyzing epoxidation reactions using the catalysts, and to methods for manufacturing the catalysts.

BACKGROUND

Although epoxidation of ethylene has been industrially applied for many years, the catalysts used typically show poor selectivity in the epoxidation of propylene. As a consequence, direct oxidation of propylene to propylene oxide with high selectivity and activity has yet to be achieved in heterogeneous catalysis.

Catalysts currently used in ethylene epoxidation often contain reduced silver and an $\alpha$-alumina carrier. Catalysts of this nature have been disclosed, for example, in U.S. Pat. No. 4,248,740 to Mitsuhata et al. and U.S. Pat. No. 4,342,667 to Armstrong et al. Other ethylene epoxidation systems have been developed using catalysts that include small amounts of alkali metals such as potassium, sodium, rubidium, and cesium that act as promoters when used in conjunction with reduced silver. U.S. Pat. No. 4,010,115 to Nielsen et al. describes such a system. A review of the direct epoxidation of ethylene in the presence of supported silver catalysts is provided by Sachtler et al. (1981) *Catalysis Reviews: Science and Engineering* 23 (1&2): 127–149.

Unfortunately, these ethylene oxidation catalysts display low selectivity in the epoxidation of propylene. While not wishing to be bound by theory, the inventors propose that the low selectivity of these catalysts can be explained by the mechanism for the formation of propylene oxide. The reaction appears to involve oxygen radicals on the surface of the silver which interact with the propylene to form an epoxide intermediate. $\alpha$-Hydrogen atoms are then removed from the intermediate by a neighboring oxygen atom, resulting in the formation of $CO_2$ rather than propylene oxide.

Attempts to improve the selectivity of propylene epoxidation catalysts have typically focused on the preparation of silver sites without the destructive neighboring oxygen radicals. The isolation of silver sites has been attempted by preparing catalysts having very small silver particles, using either zeolites, as in Giordane et al. (1981) *Z. Phys. Chem. Neue Folge* 127:109 and Jacobs et al. (1979) *J. Chem. Soc. Faraday I* 75:59, sol-gel methods, as in Breitscheidel et al. (1991) *Chem. Mater.* 3:559, or alloying of the silver with gold, as in Geenen et al. (1982) *J. Catal.* 77:499 and Toreis et al. (1987) *J. Catal.* 108:161.

Another approach to controlling the proximity of active sites is based on the idea of poisoning a specific fraction of the silver sites with either an alkali metal or a gaseous additive such as $CO_2$. Examples of this type of pretreatment are discussed in U.S. Pat. Nos. 5,856,534 and 5,780,657 to Cooker et al. Poisoning with alkyl halides has also been successfully used to improve the selectivity of propylene epoxidation catalysts, as disclosed, for example, in U. S. Pat. No. 5,770,746 to Cooker.

Modifications to the catalyst support have also been carried out in an effort to improve selectivity. Canadian Patent No. 1,282,772 describes the use of an alkaline earth metal carbonate as the exclusive support material for silver in an epoxidation catalyst for ethylene, propylene and other olefins. This catalyst does not contain any of the traditional support materials, e.g., alumina, and consequently the amount of alkaline earth metal carbonate that must be used is significantly higher than previously disclosed in the art. This catalyst system uses $KNO_3$ in combination with $NO/NO_2$ and an alkyl chloride as gas phase additives.

Various modifications of the catalyst system described in the aforementioned Canadian patent have been recently made using potassium salts and molybdenum promoters (see U.S. Pat. No. 5,625,084 to Pitchai et al.), pretreating with high temperature organic chloride and molecular oxygen steam (see U.S. Pat. No. 5,770,746 to Cooker et al.), using inorganic chloride promoters and potassium promoters, (see U.S. Pat. No. 5,780,657 to Cooker et al.), pretreating with $CO_2$ (see U.S. Pat. No. 5,856,534 to Cooker et al.), and using tungsten and rhenium promoters (see U.S. Pat. No. 5,861,519 to Kahn et al. and U.S. Pat. No. 5,864,047 to Gaffney).

The deposition of silver onto the carrier can be achieved by a number of techniques. One technique that is frequently employed involves the impregnation of the support with a silver solution followed by heat treatment of the impregnated support, to effect deposition of the silver on the support. Another common technique involves coating the silver on the support by precipitating the silver, or a preformation of silver, into a slurry and placing the support in the slurry. The slurry is then heated to remove the liquids present. As the liquids are removed, the silver particles are deposited on the support and adhere to the support surface.

Thus, the art provides propylene oxidation catalysts using alkali earth metal carbonate supports in conjunction with alkali, halogen, tungsten, and rhenium promoters and in conjunction with $CO_2$, $NO/NO_2$ and/or an alkali metal chloride as a gas phase additive. It has now been unexpectedly discovered that a catalyst that is highly selective for the direct production of propylene oxide from propylene is obtained by using an alkaline earth metal carbonate as a support in combination with a rare earth metal promoter. Also surprising is the finding that such catalysts are capable of selective propylene oxidation in the absence of the gaseous $CO_2$, $NO/NO_2$ and/or an alkyl chloride promoter that have heretofore been commonly used to improve epoxide selectivity in vapor phase processes of this type.

SUMMARY OF THE INVENTION

Accordingly, it is a primary object of the invention to provide a process for the conversion of propylene to propylene oxide having increased selectivity for propylene oxide and a higher conversion of propylene than have been obtained previously.

It is a further object of the invention to provide a composition useful as an epoxidation catalyst for use in the conversion of propylene to propylene oxide having increased selectivity for propylene oxide and a higher conversion of propylene than have been reported with the prior art.

Additional objects, advantages and novel features of the invention will be set forth in part in the description which follows, and in part will become apparent to those skilled in the art upon examination of the following, or may be learned by practice of the invention.

In a first embodiment, then, a novel process for the conversion of propylene to propylene oxide is provided wherein a propylene and oxygen-containing gas feedstream contacts an alkaline earth metal carbonate-supported silver catalyst that comprises a catalytically effective amount of silver and a promoting amount of a rare earth metal promoter.

In a second embodiment, a process for the conversion of propylene to propylene oxide is provided wherein a propylene and oxygen-containing gas feedstream contacts an alkaline earth metal carbonate supported silver catalyst that has a catalytically effective amount of silver, and a promoting amount of a rare earth metal, a halogen anion, and an alkali metal nitrate.

In a further embodiment, catalyst compositions for the conversion of propylene to propylene oxide are provided having an alkaline earth metal carbonate support, a catalytically effective amount of silver, and promoting amounts of a rare earth metal promoter.

In a still further embodiment, catalyst compositions for the conversion of propylene to propylene oxide are provided that have an alkaline earth metal carbonate support, a catalytically effective amount of silver, a promoting amount of a rare earth metal, a halogen anion, and an alkali metal nitrate.

In yet another embodiment, methods for making a catalyst composition for the conversion of propylene to propylene oxide are provided, comprising the steps of: (a) preparing a basic solution comprising an alkali metal carbonate and an alkali metal hydroxide; (b) preparing a precursor solution comprising an alkaline earth metal salt, a silver salt and a rare earth metal salt; and (c) mixing the basic solution with the precursor solution, thereby precipitating the catalyst composition.

A BRIEF DESCRIPTION OF THE DRAWINGS

FIG. 1 presents a precipitation curve obtained during catalyst synthesis, as described in Example 21.

DETAILED DESCRIPTION OF THE INVENTION

Definition and Nomenclature

Before the present compounds, compositions and methods are disclosed and described, it is to be understood that unless otherwise indicated this invention is not limited to specific support structures, reagents, methods of preparation, or the like, as such may vary. It is also to be understood that the terminology used herein is for the purpose of describing particular embodiments only and is not intended to be limiting.

It must be noted that, as used in the specification and the appended claims, the singular forms "a", "an" and "the" include plural referents unless the context clearly dictates otherwise. Thus, for example, reference to "a promoter" includes one or more promoters, reference to "a support" includes one or more supports, and the like.

The term "alkali metal" refers to elements of Group Ia of the Periodic Table, i.e., lithium, sodium, potassium, rubidium, caesium, and francium.

The term "alkali earth metal" refers to elements of Group Ia of the Periodic Table, i.e., beryllium, magnesium, calcium, strontium, barium and radium.

The term "rare earth metal" refers to elements of the lanthanide and actinide series of the Periodic Table.

For the purposes of this invention, the term "conversion" is taken to mean the mole percent of propylene lost from the feed stream as a result of reaction. Likewise, the term "selectivity to propylene oxide" is taken to mean the mole percent of reacted propylene which is used to form propylene oxide. The conversion and selectivity of the process of this invention can vary over a wide range. Process variables influencing conversion and selectivity include temperature, flow rate, concentration of oxygen, and concentration of propylene. Generally, as the concentration of propylene in the feed stream decreases, the conversion of propylene increases and the selectivity for propylene oxide decrease.

A "support" is a carrier that comprises the catalytically active components of a supported, i.e., heterogeneous, catalyst. In the present catalyst, the support is comprised of an alkali earth metal carbonate.

A "promoter" means a component that provides an improvement in one or more of the catalytic properties, e.g., selectivity, activity, conversion, stability, yield, of the catalyst as compared to a catalyst not containing the promoter. "Effective promoting amount" means an amount of a promoter sufficient to yield the above mentioned improvement.

"Halo" or "halogen" refers to fluoro, chloro, bromo or iodo, and usually relates to halide substitution for a hydrogen atom in an organic compound. Of the halides, chloro and fluoro are generally preferred.

"Optional" or "optionally" means that the subsequently described event or circumstance may or may not occur, and that the description includes instances where said event or circumstance occurs and instances where it does not. For example, the phrase "catalyst containing an optional alkali metal nitrate" means that an alkali metal nitrate may or may not be present and that the description includes catalysts that comprise an alkali metal nitrate and catalysts that do not.

The term "redox half-reaction" generally represents the transfer of an electron(s) to or from as substrate, while the companion redox half-reaction represents the transfer of said electron(s) from or to a second substrate. As used herein "redox half-reaction" refers to half-reactions such as those found in equations presented in tables of standard reduction or oxidation potentials, also known as standard or single electrode potentials, of the type found in, for instance, the Handbook of Chemistry and Physics, CRC Press, 1995, pages D155–162.

As used herein all reference to the Periodic Table of the Elements and groups thereof is to the version of the table published by the Handbook of Chemistry and Physics, CRC Press, 1995, which uses the IUPAC system for naming groups.

The Novel Catalyst

The catalyst of the invention are alkaline earth metal carbonate-supported, silver catalysts that incorporate a promoting amount of a rare earth metal promoter. The alkaline earth metal carbonate may be any carbonate of any element of Group IIa or combination of such carbonates. Suitable carbonates are described, for example, in Canadian Patent No. 1,282,772 to Thorsteinson and include, but are not limited to, calcium carbonate, barium carbonate, strontium carbonate, magnesium carbonate and mixtures thereof. Calcium and barium carbonates are preferred. The alkaline earth metal carbonate may constitute from about 40% w/w to about 60% w/w of the catalyst composition, preferably about 45% w/w to about 55% w/w of the composition.

The silver is generally, although not necessarily, precipitated in the form of silver carbonate. The metallic silver will generally be present in the range of about 35% w/w to about 50% w/w of the final catalyst, preferably, in the range of about 40% w/w to about 45% w/w of the catalyst.

The rare earth metal promoter can be selected from any of the elements of the lanthanide series, i.e., atomic number 57 to atomic number 70. Suitable promoters include, but are not limited to, lanthanum, cerium, praseodynium, gadolinium, erbium and combinations thereof. Lanthanum is preferred. The rare earth metal promoter is present in an amount in the range of about 0.1%w/w to about 20% w/w of the catalyst composition, preferably about 1% w/w to about 15% w/w and most preferably about 5% w/w to about 10% w/w of the composition.

Optionally, the catalyst may be infused with an alkali metal nitrate in addition to the alkali metal nitrates formed by the recombination of the nitrate and alkali salts used during the synthesis of the catalyst, as will be discussed below. The metal anion in the alkali metal nitrate may be selected from any of the elements of Group Ia. Preferred alkali metal anions include sodium and potassium. When included, the alkali metal nitrate is present in an amount sufficient to achieve an amount of alkali in the range of between about 0.1% w/w to about 2% w/w, preferably between about 0.3% w/w and 0.7% w/w, and most preferably about 0.5% w/w.

Halide promoters may also be present in the catalyst. Such promoters may be added to the catalyst composition in the form a alkali metal halide or other soluble halide compound, i.e., HCl. Suitable alkali metal halide promoters include, for example, sodium chloride, sodium bromide, potassium chloride and potassium bromide. Preferred alkali metal halides are sodium chloride and sodium bromide, with sodium chloride most preferred. The halide promoter may be present in an amount ranging from about 0.005 and 0.05 g Cl/g Ag, preferably from about 0.01 g Cl/g Ag to about 0.02 g Cl/g Ag. In terms of molar ratios, this represents an Cl/Ag molar ratio of about 0.015 to about 0.15, preferably between about 0.03 to about 0.06 mole Cl/mole Ag.

The catalyst may also contain an additional support element. Suitable additional supports include, but are not limited to, alumina, silica, titania, alkaline earth metal oxides, rare earth oxides, and mixtures of the above. Preferred catalysts do not contain additional support elements.

The catalyst compositions may be prepared using standard precipitation methods. Such precipitation methods are well known in the art; see, for example, U.S. Pat. No. 5,625,084 to Pitachai et al., U.S. Pat. No. 3,3836,481 to Kajimoto et al., and U.S. Pat. No. 5,618,954 to Boeck et al. A basic solution containing an alkali metal carbonate and an alkali metal hydroxide is reacted with an aqueous precursor solution containing a suitable alkaline earth metal salt, a silver salt, a rare earth metal promoter and optionally an alkali metal nitrate and an alkali metal halide promoter as discussed above. The precursor solution may be acidified using nitric acid. Acidification of the precursor solutions assists in the dissolution of the precursor salts and the solution may be acidified to a pH of about 3. Such acidification generally takes place prior to the addition of the basic solution. It should be noted that although other acids, such as HCl, may be used to acidify the solution, sulfuric acid or phosphoric acid are not favored as these acids may result in the formation of sulfates and phosphates which are not desired in the final catalyst. Organic acids are also disfavored. If HCl is used to acidify the precursor solution, it may only be added in limited amounts as the total concentration of halide in the catalyst should be in an amount ranging from about 0.005 and 0.05 g Cl/g Ag, preferably from about 0.01 g Cl/g Ag to about 0.02 g Cl/g Ag, as discussed above.

In one precipitation method, method A, the basic solution is injected by pump into the precursor solution to form a precipitation solution. The pH of the precipitation solution is monitored and the injection of the basic solution is terminated when the pH of the precipitation solution indicates that all silver and alkaline earth metal carbonates have precipitated out, generally at a pH of about 10. In a second precipitation method, method B, the basic solution and the precursor solution are simultaneously added to a separate water-containing precipitation vessel forming the precipitation solution therein. The pH of the precipitation solution is monitored and the injection rate of the basic solution is controlled so as to maintain the pH of the precipitation solution at a desired level, typically in the range of about pH 10 to about pH 12. The rate of precursor injection is held constant, generally although not necessarily in the range of about 10 mL/h to about 1000 mL/h.

During precipitation, the carbonate ion from the alkali metal carbonate interacts with the alkaline earth metal ion and the silver ion contained in the precursor solution, forming the silver-containing alkaline earth metal carbonate support, which then precipitates out of solution. Similarly the alkali metal ion from the basic solution and the nitrate and carbonate ions from the precursor and basic solutions interact to form alkali metal nitrates and carbonates. Formation of alkali carbonates from these substituents will be most favored. Promoting amounts of the rare earth metal promoter and alkali metal nitrate and alkali metal halide promoters, if included, are also contained in the resulting precipitate.

When method A is used, the components of the catalyst precipitate sequentially. It is observed that the rare earth metal promoter and the silver co-precipitate out of the solution first, as hydroxides, hydroxycarbonates, and/or carbonates, at a pH of about 7. This is followed by the alkaline earth metal carbonate, which precipitates from about pH 7.5 to about pH 8.5. When method B is used, the various components co-precipitate out of solution.

The resulting precipitate is then filtered, dried and calcined at sufficient temperature and for a sufficient time to reduce the silver precursor without decomposing the alkali metal nitrates or alkali metal halide promoters, generally at about 300° C. to about 3 50° C. for 10 to 20 minutes or less. It is important to note that the precipitate is not washed before drying and calcination in order to maintain the level of alkali present. The activity of the catalyst may be tested using a quartz flow reactor attached to an automatic sampling valve for GC analysis.

The alkali metal carbonate used in the basic solution may be any selected from potassium carbonate, sodium carbonate, rubidium carbonate or cesium carbonate or mixtures thereof. Potassium carbonate and sodium carbonate are preferred and sodium carbonate most preferred.

The alkali metal hydroxide is used to control the pH of the precipitation solution and to provide additional alkali metal ions. Suitable alkali hydroxides are sodium hydroxide and potassium hydroxide. Sodium hydroxide is preferred.

The alkaline earth metal salt may be any salt that will not adversely react with the other components utilized. Suitable salts include, but are not limited to, nitrates, nitrites, propionates, sulfates, chlorates, perchlorates and chlorites. Examples of specific alkaline earth metal salts include, but are not limited to, calcium nitrate, barium nitrate, magnesium nitrate, strontium nitrate, calcium sulfate, barium sulfate, magnesium sulfate, strontium sulfate, and combinations thereof. Barium nitrate and calcium nitrate are preferred and barium nitrate is most preferred.

The silver salt may be any salt that will not adversely react with the other components utilized. Suitable salts include, but are not limited to, nitrates, nitrites, propionates, sulfates, chlorates, perchlorates and chlorites. Examples of specific silver salts include, but are not limited to, silver nitrate, silver sulfate, silver chlorate, silver sulfate, silver nitrite, silver propionate, silver perchlorate, silver chlorite and mixtures thereof. Silver nitrate is preferred.

Another embodiment of the invention relates to a method of oxidizing propylene using the catalyst of the invention. The catalyst may be used in the direct oxidation of propylene to yield propylene oxide. The catalytic process involves contacting propylene with oxygen in the presence of a catalyst of the invention under conditions such that propylene oxide is formed.

The oxygen employed in the aforementioned process of this invention may be obtained from any gas containing molecular oxygen, such as air, commercially pure oxygen or other substances that under epoxidation conditions exists in a gaseous state and forms molecular oxygen. The propylene and oxygen are present as a propylene and oxygen-containing gas feedstream in amount sufficient to allow formation of the propylene oxide. Preferably the concentration of propylene in the feedstream is in the range of about 2% v/v to about 25% v/v, with concentrations ranging from about 5% v/v to about 20% v/v being preferred and concentrations ranging from about 8% v/v to about 17% v/v.

The feedstream may also contain a gaseous efficiency-enhancing member of a redox-half reaction and a gas phase halogen compound, such as an alkyl halide. The preferred gaseous efficiency-enhancing materials are compounds containing an element capable of existing in more than two valence states, preferably nitrogen, and another element that is preferably oxygen. Examples of preferred gaseous efficiency-enhancing members of a redox-half reaction pair include, but are not limited to, at least one of NO, $NO_2$, $N_2O_4$, $N_2O_3$ or any gaseous substance capable of forming one of the aforementioned gases, particularly NO and $NO_2$, under epoxidation conditions. NO is most preferred. The gaseous efficiency-enhancing member of a redox-half reaction is typically present in concentrations ranging from about 0.1 to about 2,000 ppm. Concentrations ranging from about 1 to about 1000 ppm are preferred and concentrations ranging from about 50 to about 500 ppm are most preferred.

The gas phase halogen compound is preferably an organic halide, saturated or unsaturated, such as ethylene dichloride, ethyl chloride, vinyl chloride, methyl chloride and methylene chloride. Ethyl chloride is preferred. The gas phase halogen compound is typically present at a concentration ranging from about 0.1 to about 2,000 ppm. Concentrations ranging from about 1 to about 1000 ppm are preferred and concentrations ranging from about 50 to about 100 ppm are most preferred.

The remainder of the feedstream may be made up of an inert gas such as nitrogen or helium as a ballast or diluent. Varying amounts of carbon dioxide and water vapor may also be present, depending upon whether means have been provided to remove such substances from the feedstream components. It is preferred that no carbon dioxide be present in the feedstream as the inclusion of carbon dioxide tends to result in lower selectivity.

The reactants can be contacted with the catalyst in any suitable reactor. Tubular stainless steel reactors designed to withstand the pressure and temperature of the reaction are preferred. While the reaction can take place in either the gaseous phase or in a liquid solvent, contact in the gaseous phase is preferred. The oxygen/propylene feed stream is preferably preheated to a temperature about that of the reaction temperature. The reaction can occur at any operable temperature upon contacting the catalyst and the reactants. Generally temperatures are above 50° C. and preferred temperatures are in the range of about 200° C. to about 500° C. with temperatures in the range of about 200° C. to about 400° C. most preferred. The pressure and temperature should be adjusted to achieve optimal results for the particular catalyst and feedstream being used. Generally pressures range from about 1 to about 30 atmospheres with atmospheric pressure being preferred.

The reaction time, i.e., the duration of time the reactants remain in contact with the catalyst, must be sufficient to allow for oxidation of the propylene. Generally, the duration of the contact varies according to the size of the reactor and the amount of catalyst used. Contact time is controlled by varying the gas hourly space velocity of the feedstream as it passes through the reactor. Generally, space velocities in the range of from about 10 $hr^{-1}$ to about 15,000 $hr^{-1}$ are suitable. Space velocities in the range of from about 100 $hr^{-1}$ to about 6,000 $hr^{-1}$ are preferred and space velocities in the range of from about 500 $hr^{-1}$ to about 3,000 $hr^{-1}$ are most preferred.

The propylene oxide reaction product is a useful industrial intermediate, particularly in the manufacture of urethane polymers. Propylene oxide is also useful in the production of propylene glycol, which is used to form plastics, and in the production of propene glycol ethers, which are used as solvents.

Typically, the catalyst of this invention produces an olefin conversion of at least about 0.1 percent. Preferably, the catalyst produces a conversion greater than about 0.2 percent; more preferably a conversion greater than about 0.5 percent, and most preferably, greater than about 1.0 percent. Typically, the catalyst of this invention produces a selectivity to olefin oxide greater than about 20 percent, preferably greater than about 40 percent; more preferably greater than about 50 percent, and optimally, greater than about 60 percent.

EXPERIMENTAL

It is to be understood that while the invention has been described in conjunction with the preferred specific embodiments thereof, that the foregoing description is intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

Example 1

Preparation of Catalyst

A catalyst of the invention was prepared according to the following method. A basic solution containing 4 g/L NaOH and 60 g/L $K_2CO_3$ in purified water was prepared and injected using a Gilson Minipuls 3 peristaltic pump at a rate of 50 mL/h with vigorous stirring into a 250-mL precursor solution containing 5 g $Ca(NO_3)_2.4H_2O$, 0.5 g $La(NO_3)_2.6H_2O$ and 2.5 g $AgNO_3$ in purified water. The pH of the reaction solution was monitored using an ORION EA940 pH indicator. A brown/yellow precipitate formed. The precipitation was complete in 50 minutes and injection of the basic solution was stopped at a final pH of 10. The precipitated catalyst was filtered and dried at 160cC for 30 minutes. The catalyst was then calcined in static air at 375° C. for 15 minutes.

Example 2

Alternative Preparation of Catalyst

A catalyst of the invention was alternatively prepared according to the following method. A basic solution containing 1 g NaOH and 15 g of $K_2CO_3$ in 250 mL of purified water was prepared. A precursor solution containing 1 g $La(NO_3)_2$ $6H_2O$, 2.5 g $AgNO_3$, and 5 g $Ca(NO_3)_2$. $4H_2O$ in 150 mL of purified water was also prepared. Each solution was then injected into a separate precipitation vessel using Gilson Minipulse 3 peristaltic pumps. The precursor solution was injected at a rate of 100 mL/h and the basic solution was injected at varying rates in order to maintain the pH of the resulting precipitation solution at pH 11. The pH of the precipitation solution was continuously monitored by computer, and the speed of the base pump adjusted accordingly. The resulting catalyst precipitate was filtered, dried and calcined according to the method of Example 1.

Example 3

Alternative Catalyst Preparation

A catalyst of the invention was alternatively prepared according to the following procedure. A basic solution containing 1 g NaOH and 15 g of $K_2CO_3$ in 200 mL of purified water was prepared. A precursor solution having a pH of 4.0 was prepared by first dissolving 3.5 g $Ba(OH)_2$ in HNO3 and then dissolving 1 g $La(NO_3)_2.6H_2O$ and 2.5 g $AgNO_3$. The basic solution was then injected into the precursor solution using a Gilson peristaltic pump at a rate of 50 mL/h with vigorous stirring. A beige precipitate formed. The precipitation was complete in 50 minutes and injection of the basic solution was stopped at a final pH of 10. The precipitated catalyst was filtered and dried at 160° C. for 30 minutes. The catalyst was then calcined in flowing air at 325° C. for 15 minutes.

Example 4

Alternative Catalyst Preparation

A catalyst of the invention was alternatively prepared according to the method of Example 3. The basic solution contained 1 g NaOH and 11.5 g of $Na_2CO_3$ in 200 mL of purified water and the precursor solution contained 3.5 g $Ba(OH)_2$, 1 g $La(NO_3)_2.6H_2O$, 30 mg NaCl, 5 g $NaNO_3$, and 2.5 g $AgNO_3$. The basic solution was injected into the precursor solution at a rate of 50 mL/h. A brownish precipitate formed. The precipitated catalyst was filtered and dried at 160° C. for 30 minutes and then calcined in flowing air at 325° C. for 15 minutes.

Example 5

Activity Testing

The activity of any of the catalyst of Examples 1–4 can be tested according to the following method. 2.5 g of 20 to 48 mesh catalyst is placed in a quartz flow reactor, with of flow of 40 mL/min of 10% propylene, 5% $O_2$, 500 ppm NO, 100 ppm ethyl chloride and balance He, at atmospheric pressure. Space velocity was 1200 $h^{-1}$. The hydrocarbon/oxygen gas mixture composition is controlled using electronic mass flow controllers. The effluent from the reactor is led through a heated transfer line in to an automating sampling valve for GC analysis. The GC includes column switching between a 1-foot HP 13X molecular sieve column and an Alltech Hayesep D 100/12 column, to optimize the separation of both fixed gases and higher hydrocarbons. A flame ionization detector (FID) was place in series with a thermal conductivity detector (TCD) to provide better quantification of hydrocarbons, especially those present in low concentrations (below 1 vol. %). The response factors for the various gases (CO, $CO_2$, $C_3H_8$, $C_3H_6$, propylene oxide, and $C_2$ species) for both detectors were determined, for quantification purposes and to allow calculation of mass balances. The composition of product streams was also confirmed by mass spectroscopy, using a Dycor Quadlink spectrometer.

Examples 6–16

Catalyst Conversion and Selectivity

The following catalysts were prepared according to the methods described in Examples 1–3 and their activity assessed according to the method described in Example 5. The results presented were obtained after 3 hours of reaction time.

TABLE 1

Catalyst Activity

| Example | Catalyst | Temperature (° C.) | % Conversion | % Selectivity |
|---|---|---|---|---|
| 6 | 45% Ag/53% $CaCO_3$/2% La | 230 | 3 | 37 |
| 7 | 44% Ag/52% $CaCO_3$/4% La | 240 | 4 | 38 |
| 8 | 42% Ag/51% $CaCO_3$/7% La | 265 | 4 | 47 |
| 9 | 40% Ag/46% $CaCO_3$/14% La | 230 | 3–4 | 28 |
| 10 | 42% Ag/51% $BaCO_3$/7% La | 265 | 7–10 | 52 |
| 11 | 43% Ag/49% $MgCO_3$/8% La | 265 | 6 | 10 |
| 12 | 43% Ag/50% $SrCO_3$/7% La | 265 | 4 | 11 |
| 13 | 44% Ag/53% $CaCO_3$/3% Ce | 220 | 12 | 7 |
| 14 | 43% Ag/50% $CaCO_3$/7% Gd | 265 | 3 | 39 |
| 15 | 40% Ag/46% $CaCO_3$/7% Er | 240 | 3 | 11 |
| 16 | 40% Ag/52% $CaCO_3$/8% Pr | 235 | 3 | 9 |

Examples 17–20

Catalyst Conversion and Selectivity

The following catalysts were prepared according to the method described in Example 4 and their activity assessed according to the method described in Example 5. The results presented in Table 2 were obtained after 3 hours of reaction time.

TABLE 2

Catalyst Conversion and Selectivity to Propylene Oxide

| Example | Catalyst | Temperature (° C.) | % Conversion | % Selectivity |
|---|---|---|---|---|
| 17 | Ag/$KNO_3$/La/$CaCO_3$ | 250 | 4.4 | 40 |
| 18 | Ag/Cl/$KNO_3$/La/$CaCO_3$ | 250 | 2.4 | 45 |
| 19 | Ag/Cl/$KNO_3$/La/$BaCO_3$ | 250 | 1.6 | 57 |
| 20 | Ag/Cl/$NaNO_3$/La/$BaCO_3$ | 250 | 1.0 | 65 |

Example 21

Precipitation Curve

The precipitation curve presented as FIG. 1 was obtained using the method of Examples 1–3. The precipitation was conducted by injecting a solution containing 4 g/L NaOH and 60 g/L $K_2CO_3$ at 50 mL/h into a 250 mL solution of 5 g $Ca(NO_3)_2.4H_2O$ and 2.5 g $AgNO_3$, with vigorous stirring. The pH changes as a function of the amount of base solution injected and the amount of remaining Ag+ and Ca+ present in the solution. When the precipitation rate equals the rat of base(carbonate) injection, the pH attains a constant value.

What is claimed is:

1. A process for the conversion of propylene to propylene oxide comprising contacting at a temperature in the range of about 200° C. to about 500° C.:
   (i) a feedstream comprising propylene and an oxygen-containing gas; and
   (ii) a supported silver catalyst comprising
      (a) an alkaline earth metal carbonate support;
      (b) a catalytically effective amount of silver; and
      (c) a promoting amount of a lanthanide metal promoter, effective to improve selectivity to propylene oxide.

2. A process of claim 1, wherein the catalyst is prepared by precipitation.

3. A process of claim 1, wherein the feedstream is essentially free of carbon dioxide.

4. The process of claim 1, wherein the lanthanide metal promoter is lanthanum.

5. The process of claim 1, wherein the alkaline earth metal carbonate support is selected from the group consisting of strontium carbonate, calcium carbonate, barium carbonate and mixtures thereof.

6. The process of claim 5, wherein the alkaline earth metal carbonate is a barium carbonate support.

7. A process for the conversion of propylene to propylene oxide comprising contacting at a temperature in the range of about 200° C. to about 500° C.:
   (i) a feedstream comprising propylene and an oxygen-containing gas; and
   (ii) a supported silver catalyst comprising
      (a) an alkaline earth metal carbonate support;
      (b) a catalytically effective amount of silver;
      (c) a promoting amount of a lanthanide metal promoter effective to improve selectivity to propylene oxide;
      (d) an effective promoting amount of an alkali metal halide; and
      (e) an effective promoting amount an alkali metal nitrate.

8. A process of claim 7, wherein the catalyst is prepared by precipitation.

9. A process of claim 7, wherein the feedstream is essentially free of carbon dioxide.

10. The process of claim 7, wherein the lanthanide metal promoter is lanthanum.

11. The process of claim 7, wherein the alkaline earth metal carbonate support is selected from the group consisting of strontium carbonate, calcium carbonate, barium carbonate and mixtures thereof.

12. The process of claim 11, wherein the alkaline earth metal carbonate support is a barium carbonate support.

13. The process of claim 7, wherein the alkali metal halide is sodium chloride.

14. The process of claim 7, wherein the alkali metal nitrate is sodium nitrate.

15. A catalyst composition comprising:
   (a) an alkaline earth metal carbonate support;
   (b) a catalytically effective amount of silver, and
   (c) a promoting amount of a lanthanide metal promoter effective to improve selectivity to propylene oxide.

16. The catalyst composition of claim 15, wherein the catalyst composition is prepared via precipitation.

17. The catalyst composition of claim 15, wherein the lanthanide metal promoter is lanthanum.

18. The catalyst composition of claim 15, wherein the alkaline earth metal carbonate support is selected from the group consisting of strontium carbonate, calcium carbonate, barium carbonate and mixtures thereof.

19. The catalyst composition of claim 18, wherein the alkaline earth metal carbonate support is a barium carbonate support.

20. A catalyst composition comprising:
   (a) an alkaline earth metal carbonate support;
   (b) a catalytically effective amount of silver;
   (c) a promoting amount of a lanthanide metal promoter effective to improve selectivity to propylene oxide;
   (d) an effective promoting amount of an alkali metal halide; and
   (e) an effective promoting amount an alkali metal nitrate.

21. The catalyst composition of claim 20, wherein the catalyst composition is prepared via precipitation.

22. The catalyst composition of claim 20, wherein the lanthanide metal promoter is lanthanum.

23. The catalyst composition of claim 20, wherein the alkali metal halide is sodium chloride.

24. The catalyst composition of claim 20, wherein the alkali metal nitrate is sodium nitrate.

25. The catalyst composition of claim 20, wherein the alkaline earth metal carbonate support is selected from the group consisting of strontium carbonate, calcium carbonate, barium carbonate and mixtures thereof.

26. The catalyst composition of claim 25, wherein the alkaline earth metal carbonate support is a barium carbonate support.

27. A catalyst comprising about 40% w/w to about 60% w/w alkaline earth metal carbonate, about 35% w/w to about 50% w/w silver, and about 1% w/w to about 15% w/w rare earth metal promoter.

28. The catalyst of claim 27, comprising about 45% w/w to about 55% w/w alkaline earth metal carbonate, about 40% w/w to about 45% w/w silver, and about 5% w/w to about 10% w/w rare earth metal promoter.

29. The catalyst of claim 27, further comprising about 0.1% w/w to about 2% w/w alkali metal halide.

30. A method of making a catalyst comprising:
   a. preparing a basic solution comprising an alkali metal carbonate and an alkali metal hydroxide;
   b. preparing a precursor solution comprising an alkaline earth metal salt, a silver salt, and a rare earth metal salt; and
   c. mixing the basic solution with the precursor solution, thereby precipitating the catalyst.

31. The method of claim 30, wherein the precursor solution further comprises an alkali metal nitrate.

32. The method of claim 30, wherein the precursor solution further comprises an alkali metal halide.

33. The method of claim 30, wherein the basic solution and the precursor solution are mixed by injecting the basic solution into the precursor solution and the catalyst forms by sequential precipitation of silver and carbonate compounds.

34. The method of claim 30, wherein the basic solution and the precursor solution are mixed by simultaneously injecting the basic solution and the precursor solution into a separate flask.

* * * * *